United States Patent [19]

Hirschman

[11] 4,196,562

[45] * Apr. 8, 1980

[54] METHODS OF MAKING FEMININE HYGIENIC PADS WITH ANTERIOR LEADING EDGES

[76] Inventor: Shalom Z. Hirschman, 110-11 Queens Blvd., Forest Hills, N.Y. 11375

[ * ] Notice: The portion of the term of this patent subsequent to Jun. 20, 1995, has been disclaimed.

[21] Appl. No.: 874,632

[22] Filed: Feb. 2, 1978

Related U.S. Application Data

[63] Continuation-in-part of Ser. No. 732,941, Oct. 15, 1976, Pat. No. 4,095,542.

[51] Int. Cl.² .................. A61F 13/18; D06M 17/00; B32B 1/10
[52] U.S. Cl. ........................ 53/450; 128/270; 128/285; 156/227; 156/200; 156/204; 156/213; 156/217; 156/73.1; 28/116; 53/456; 270/57; 270/62
[58] Field of Search ............... 156/217, 218, 203, 227, 156/226, 73.1, 213, 200, 204; 128/285, 290 P, 270, 295; 112/262; 53/450, 456; 28/116, 118, 119, 120; 270/57, 62

[56] References Cited

U.S. PATENT DOCUMENTS

| | | | |
|---|---|---|---|
| 2,515,321 | 7/1950 | Stanley | 112/401 |
| 2,668,296 | 2/1954 | Welch | 112/401 |
| 3,533,865 | 10/1970 | Bocquet et al. | 156/73.4 |
| 3,575,767 | 4/1971 | Banks | 128/290 P |
| 3,726,277 | 4/1973 | Hirschman | 128/285 |
| 4,057,061 | 11/1977 | Ishikawa | 128/290 P |
| 4,095,542 | 6/1978 | Hirschman | 112/262 |

*Primary Examiner*—John T. Goolkasian
*Assistant Examiner*—William H. Thrower
*Attorney, Agent, or Firm*—Arthur T. Fattibene

[57] ABSTRACT

Methods of making feminine hygienic pads from non-layered and layered material by use of folding, pressure molding and various methods of bonding to create a long geometric form with an anterior leading panel of narrow thickness and a thicker posterior underpanel of a wider thickness. The folded panels may be bonded by either a suitable adhesive, crimping, heat, pressure or ultrasonic means leaving an anterior portion with a leading anterior edge and a larger posterior portion. A filler may be inserted between the folds of the material prior to bonding. Thereafter, the long geometric form is multiple cut transversely providing pads about two inches long. These pads are used for insertion into the female interlabial space. The geometric configuration of the pads facilitates insertion of the pad via the anterior leading edge into the interlabial space and has improved retention within such space.

18 Claims, 29 Drawing Figures

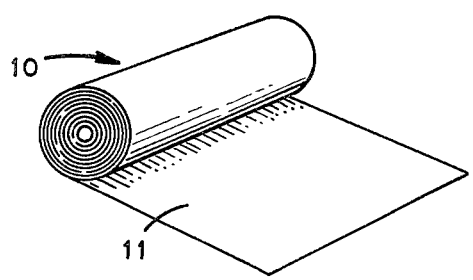
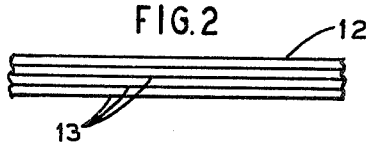
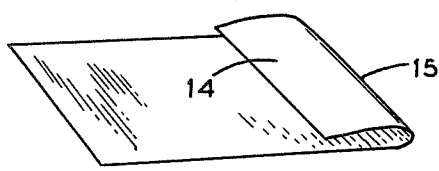
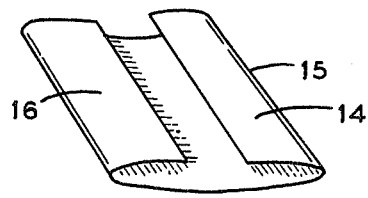
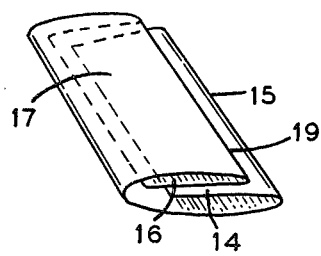
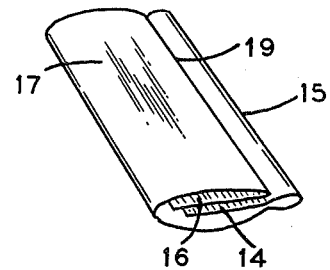
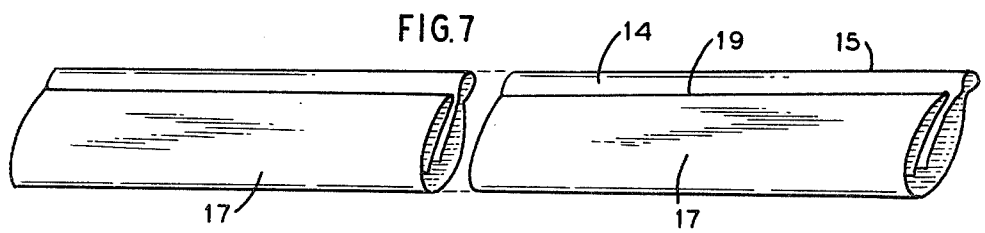
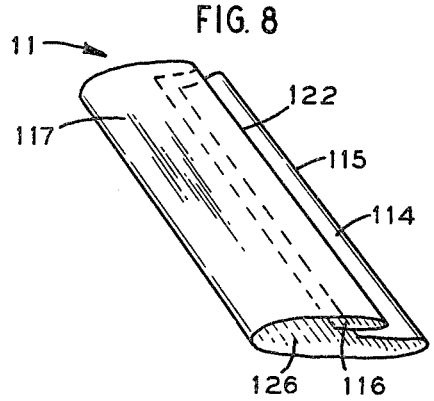
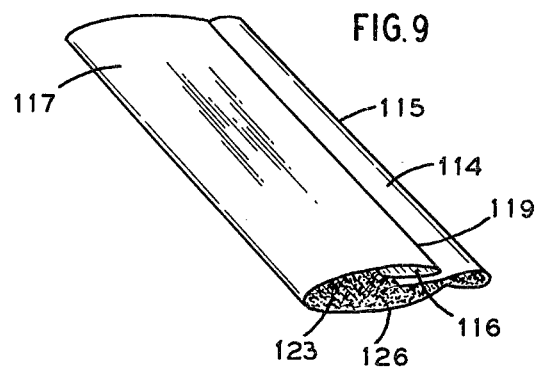

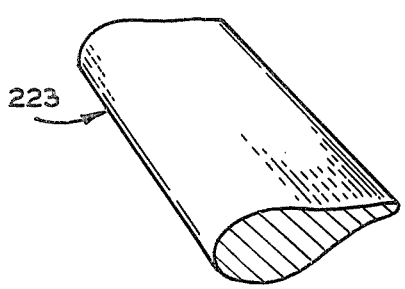
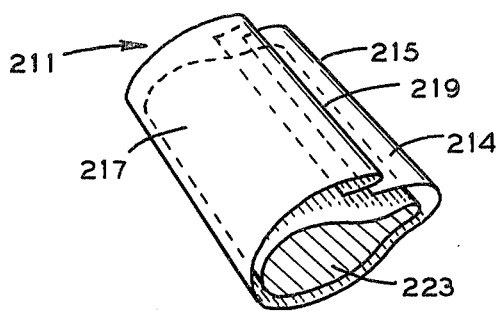
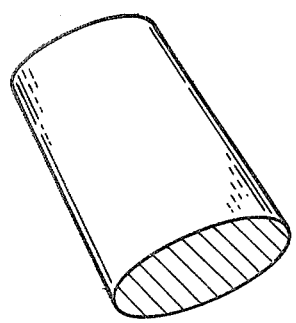
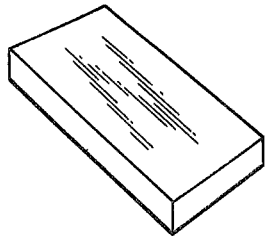
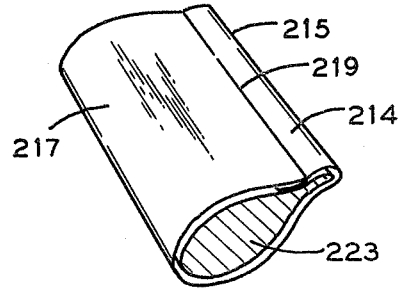
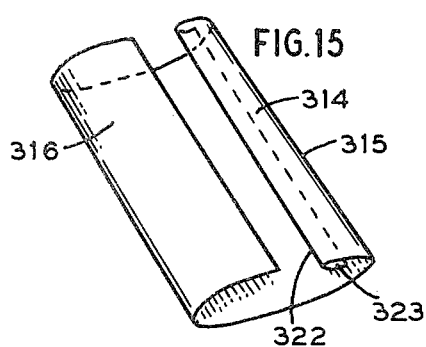
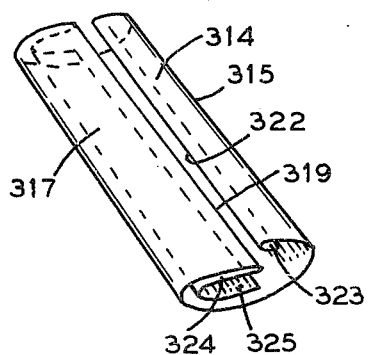
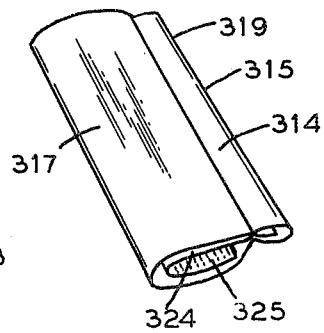
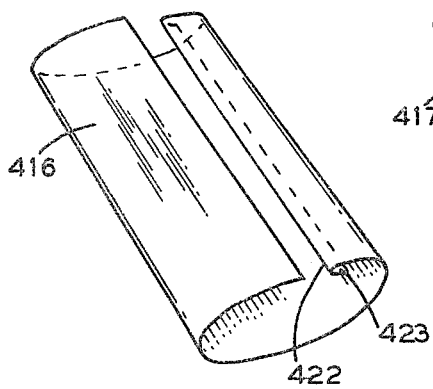
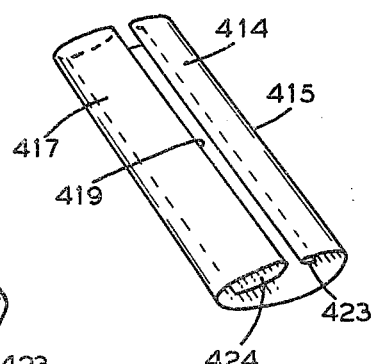
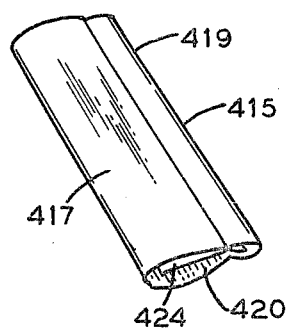

METHODS OF MAKING FEMININE HYGIENIC PADS WITH ANTERIOR LEADING EDGES

BACKGROUND OF THE INVENTION

This application is a continuation-in-part of applicants Ser. No. 732,941 filed Oct. 15, 1976, now U.S. Pat. No. 4,095,542, issued June 20, 1978.

Applicant has created a number of feminine hygienic pads for use by females to absorb uncontrolled discharges, such as urine, vaginal secretions, post-coital leakage, menstrual staining, or the like as shown and described in his U.S. Pat. Nos. 3,726,277 and 3,983,873.

Such pads must be carefully made of certain soft layered or non-layered materials and in some versions with filler materials so that certain dimensions of the pads are maintained. Such pads have been difficult and relatively expensive to produce.

An object of this invention is to provide a method, or methods of producing feminine hygienic pads inexpensively maintaining desired dimensions and characteristics of the pad so that the female may place such pad into the interlabial space easily and quickly to absorb uncontrolled discharges, such as urine, vaginal secretions or the like.

The methods used to create such pads must provide an inexpensive pad having certain geometric cross sections distiguished by anterior leading edge portions of increased stiffness or reduced transverse thickness and posterior portions of greater or more substantial transverse thickness, and increased absorptive capacity. The desired dimensions and geometric configuration must be substantially maintained during quantity production. The methods of applicant accomplish such objects and results.

Other objects of this invention will in part be obvious and in part hereinafter pointed out.

DESCRIPTION OF THE DRAWINGS

FIG. 1 is a perspective view of a roll of layered material used in the making of the hygienic pads;

FIG. 2 is an enlarged sectional view of a four layered material of the roll of material shown in FIG. 1.

FIG. 3 is a perspective view of one fold of the layered material;

FIG. 4 is a perspective view of another fold of the layered material;

FIG. 5 is a perspective view of the folded material folded upon itself leaving a longitudinal narrow panel and leading edge;

FIG. 6 is a perspective view of the folded material shown in FIG. 5 bonded adjacent its leading edge creating the complete geometric form of the first version of the pad;

FIG. 7 is a perspective view of the long pad after folding and bonding but before it is cut into the desired pad lengths;

FIG. 8 is a perspective view of another or second form of the material showing the manner of folding such material during the method of making the pad;

FIG. 9 is a perspective view of the material folded in four panels, shown in FIG. 8, wrapped around a filler and bonded together finished as a pad;

FIG. 10 is a perspective view of a pre-shaped pad of pressed material used as an inner core for a pad;

FIG. 11 is a perspective view of the score shown in FIG. 10 with a folded material wrapped around the core prior to bonding the ends together;

FIG. 12 is a perspective view of the core shown in FIG. 10 and the outer folded material bonded and finished as a pad;

FIGS. 13 and 14 are perspective views of other pre-shaped pads of pressed material that may be used as inner cores for the pad in place of the core shown in FIG. 10;

FIG. 15 is a perspective view of another form of the material showing the manner of folding such material during the method of making the pad;

FIG. 16 is a perspective view of the material as the next step of the folding operation;

FIG. 17 is a perspective view of the folded material of FIG. 16 bonded together at its abutting edges creating the complete geometric form of such other version of the pad;

FIG. 18 is a perspective view of another form of the material showing the manner of folding such material during the making of this pad;

FIG. 19 is a perspective view of the material as the next step of the folding operation;

FIG. 20 is a perspective view of the folded material of FIG. 19 bonded together at its abutting edges creating the complete geometric form of this version of the pad;

DESCRIPTION OF THE PREFERRED METHODS

Figure 21:
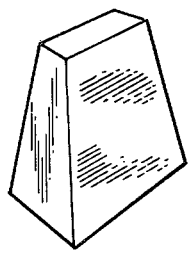
FIGS. 21, 22 and 23 are perspective views of pre-shaped pads of pressed material, namely trapezoidal, polyhedral and cylindrical in shape that may also be used as inner cores for the pad in place of the pads shown in FIGS. 10, 13 and 14.

In the first method of making hygienic pads, with anterior leading edges, a flat piece of material, which may be layered or non-layered, comes off a roll 10 or a folded bale generally made of about forty-two or sixty inches wide; however, such rolls of material may be made in any width desired. The material is then cut to about 2¼ inches wide, as shown in FIG. 1. Two methods of cutting may be used, namely material of roll 10 may be cut laterally from the material as it is unrolled, or longitudinally through the roll. The material 11 of roll 10 is preferably comprised of four or eight plies of suitable cotton gauze, cellulose, synthetic materials, or blends, such as of cotton and cellulose fibers as shown in FIG. 2. The flat material 11 may be a suitable thickness, such as 1.5 of 1/32 inch for four ply and 3/32 inch for eight ply material with an outer layer, for example, of cotton gauze 12 and inner layers 13 of pressed cotton, or other cellulose fibers as shown in FIG. 2.

The steps of the method consist of folding the material along its right longitudinal end about 5/8 inch, as shown in FIG. 3 to create a panel 14 and an anterior leading edge 15. Another fold is made at the left longitudinal end about ½ of an inch wide, as shown in FIG. 4, to create the first part of the outer panel or body 16. The panel 16 and the material beneath it is folded over again to provide the posterior panel or portion 17, as shown in FIG. 5. A folding attachment (not shown) makes the folds hereinbefore described automatically. Such folding machines are well known in the art and a special attachment for the special dimensions and number of folds desired can be readily made. Other known attachments (not shown) but known in the art of applying adhesives may be attached to the machine for simultaneous feeding a suitable adhesive, such as a mucilage beneath to the underlying material the leading edge 19 of the posterior panel or portion 17 to bond said posterior panel 17 inwardly of the anterior leading portion to define the leading anterior edge and a larger posterior portion. Other means of bonding the posterior edge portion 19 to the anterior portion 15 inwardly of the leading edge 15 may be used, such as different known adhesives, crimping, heat, pressure, ultrasonic means and the like thus creating the fixed anterior leading edge 15 about ⅛ inch in width to complete the geometric form as shown in FIG. 6. Ultrasonic bonding, crimping or pressure sealing are especially suited for creating the narrow anterior leading edge of the pad.

Since the material used is taken from the roll of material 10, shown in FIG. 1, the folded and bonded unit consists of a long pad, as shown in FIG. 7 which is then cut into small pads 2 inches in length, as shown in FIG. 6. These short pads, shown in FIG. 6, are then ready for further processing and eventual packing for delivery to the distributors.

In another method of folding the material, the panel 14 is created by folding the material along its right longitudinal end about ⅝ of an inch, as shown in FIG. 3, but the panel 16 is created by making a fold at the left longitudinal end about one inch wide. The panel 16 and the material beneath it is folded over again upon itself to provide the posterior portion 17 which is now comprised of five filler panels instead of the four filler panels shown in FIGS. 5 and 6.

Pads of varying numbers of filler panels in the posterior portion 17 and the anterior portion 14 can be created by varying the numbers of folds along the right longitudinal end and the left longitudinal end of the material. For example, a pad with six filler panels in the posterior portion 17 can be created by folding the left longitudinal end of the material 1¼ inches and folding over again on itself to create a panel ⅝ of an inch wide. The right longitudinal end is folded as described in FIGS. 4 and 5 to provide a posterior portion 17 with six filler panels.

The widths of the folds made along the right and the left longitudinal ends of the material can also be varied to create pads with various numbers of filler panels and varying curvilinear and planar cross-sections of varied thicknesses and pliabilities.

Figure 22:
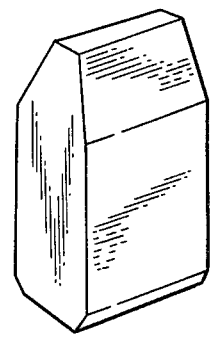
Figure 23:
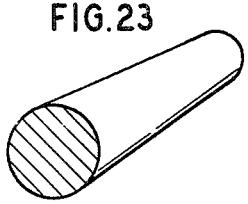
Figure 24:
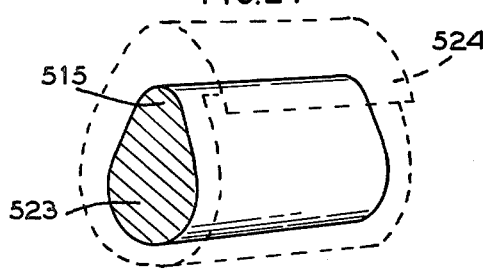
FIG. 24 is a perspective view of a pad comprised of a filler core in the process of receiving an outer wrapping.

In a second form of pad, the folding process of making the pad is shown in the steps illustrated in FIGS. 8 and 9. The material comes commercially in a roll similar to roll 10 and may be folded over cotton, cellulose, rayon or polyester filler 123 to increase the absorptive capacity of the pad. In such form, as shown in FIG. 9, where the filler material is used, the outer wrapping material 11 may have fewer layers of the fiber so that the resultant pad is not too thick. Thus, the material and method used for making such interlabial feminine hygienic pads is similar to the first method above described, except that the filler is introduced into the material as it is being automatically folded and before the material is bonded together. The filler core may be absorbent or pressed material such as cotton, cellulose, viscose, rayon, polyester or similar fibers and may be preferably of an egg shaped cross section, as shown in FIG. 10, elliptical as shown in FIG. 13, rectangular as shown in FIG. 14, trapezoidal as shown in FIG. 21, polyhedral as shown in FIG. 22, and cylindrical as shown in FIG. 23.

In the form shown in FIG. 8, the material 11 is about 1⅜ inches wide. The material 11 is folded along its right longitudinal end about ¼ inch creating a panel 114 and an anterior leading edge 115. At the left end, a fold 122 is made about ⅛ inch in width from the fold 122 to create the underneath panel 116 as part of the outer or posterior panel or body 117. The filler material 123 is fed onto the panel 126, which is part of both the posterior and anterior portions, just before the outer or posterior panel 117 with its underneath panel 116 folded over the filler 123 and the outer or posterior panel 126 and is bonded by use of an adhesive or other means hereinbefore mentioned, inside the fold 122 or along the longitudinal end surface of panel 114 leaving about ⅛ inch from the anterior leading edge 115, thus fastening the edge 119 of the posterior portion to panel 114 and creating the anterior leading panel 114 and edge 115 to complete the geometric form shown in FIG. 9. When incorporated into the anterior portion, smaller amounts of filler may be used than for the thicker posterior portion. The long pad with the filler therein, of which FIG. 9 shows a small portion, is cut in about two inch lengths and is about ⅝ of an inch in width and comprises the finished interlabial feminine hygienic pad. These pads are packed in desired containers for delivery to distributors.

It is within the scope of this invention to use a preshaped pad made from pressed cotton, cellulose, rayon or like material which is wrapped with a layer of gauze or cotton like material. In FIGS. 10, 13, 14, 21, 22 and 23, there is shown pre-shaped form 223. Cotton gauze material 211 is wrapped around the form 223 as shown in FIG. 11. The wrapped forms are shown in FIGS. 11, 12, 24 and 25 which are other forms of the invention. The form shown in FIGS. 11 and 12 has the edge 219 of the posterior portion or panel 217 bonded about ⅛ inch from the anterior leading edge 215 creating a narrow leading thin panel 214. Instead of using form 223, such preshaped forms as shown in FIGS. 13, 14, 21, 22 or 23 may be used. The material that wraps around the inner core, such as 223, is about 1⅜ inches in width. The first left fold is about ⅛ of an inch wide; the next outer adjacent portion is about ½ inch wide, the outer portion falling below the opposite outer portion is about ⅝ of an inch wide and the last right fold is about ¼ of an inch in width. The pad is about ⅜ of an inch thick, about ⅝ of an inch wide and about two inches long. The outer wrapping may have only free edges such as 524 that are wrapped around a filler core such as 523 and bonded to complete the pad. The length of the inner cores shown in FIGS. 10, 13, 14, 21, 22 and 23 are preferably of the same length as the outer wrapping. The long geometric form, hereinbefore described, is cut into lengths of about two inches. The wrapping such as 211 is held in place by pressure, crimping, heat, ultrasonic means or by some non-toxic binder like a mucilage made from a wheat flour. The core is preferably pre-pressed into the desired shapes shown in FIGS. 10, 13, 14, 21, 22 and 23, or other preferred desired geometric shapes. The long strips of the core are then wrapped around with cotton gauze or other suitable cover which must be soft, non-irritating, non-fraying and absorbent similar to the showing in FIGS. 11 and 12. A light layer of natural mucilage, for example, may be applied to the edge of the wrapping material such as 524 which is wrapped around the core 523 and the leading edge 515 to hold it in place. When the long strips are completed, such strips are then cut horizontally or transversely into the desired lengths to form the finished pads.

In FIGS. 15, 16 and 17, another form of the pad is shown which is made by folding under the material 11, which is about 2 5/16 inches wide, along its right longitudinal end about 1/16 of an inch in width to create a folded very narrow inner panel 323. The material at the right end is again folded forming a longitudinal anterior narrow panel 314 having an edge 322 and an outer leading edge 315. Panel 323 underlies panel 314. Another fold is made at the left longitudinal end about one inch in width, as shown in FIG. 15 to create the first part of the outer panel or body 316. The panel 316 and the material beneath it is folded over again upon itself to provide the posterior panel or portion 317, as shown in FIGS. 16 and 17, creating a leading edge 319 with two longitudinal panels 324 and 325 beneath the posterior panel 317.

Edges 319 and 322 are positioned so that they abut one another. As shown in FIG. 17, the two abutting edges 319 and 322 are bonded together creating the anterior narrow leading panel 314 with its leading edge 315 and the filler panels 324 and 325 between the posterior portions 317, as shown in FIG. 17. The bond at the abutting edges can be made to extend through the underlying material.

In FIGS. 18, 19 and 20, another form of the pad is shown which is similar in all respects to the previous form mentioned as shown in FIGS. 15, 16 and 17, except that panel 325 is eliminated. This method is suited for wrapping around a filler as shown in FIGS. 8 through 14 and FIGS. 21, 22 and 23. All the parts are numbered in a similar manner to the parts shown in FIGS. 15, 16 and 17 except that such parts bear the numbers in the 400's instead of the 300's. The width of the material 11 used in this last form is about 1 13/16 of an inch instead of 2 15/16 of an inch used in the previous form of the pad shown in FIGS. 15, 16 and 17. Panel 423 is about 1/16 of an inch in width, panel 414 is about ⅛ of an inch in width and panel 417 is about ½ of an inch in width. The total width of the finished pad, as shown in FIG. 20 is about ⅝ of an inch and the length is about two inches.

The outer wrapping material for making the pad may be cotton, cellulose, rayon, polyester or synthetic materials having gauze-like properties.

When using unlayered material which is very thin instead of layered material, the folding processes are the same as hereinbefore described except that the material may be pre-folded several times to provide the desired thickness. Unlayered material may be preferred for wrapping around a filler material.

When cutting the material and the pads to desired length, the type of cut can be pressed cut with some pinking so as to minimize the fraying at the cut edges.

It will be understood that the dimensions set forth above may be varied to some extent and that the method steps may also be varied, such as making the folds by means other than an automatic sequential folding, filling and bonding operation and that when folding is mentioned, it would include rolling of the material to achieve the desired folding.

It is also to be understood that if a mucilage is used as the bonding agent, such mucilage may be of a thermosetting type. Alternately, as hereinbefore stated, pressure sealing, thermal sealing or ultrasonic sealing of the edges of the wrapping may be employed. Also the cores may be either pre-pressed as shown in FIGS. 10, 13, 14, 21, 22 and 23, and as hereinbefore stated may be either pre-pressed, or may be a loose filler of cotton, cellulose, rayon, polyester, or like materials.

Figure 26:
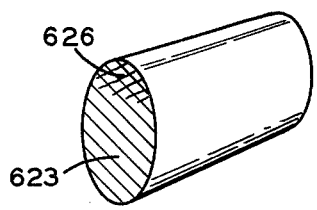
FIG. 26 is a perspective view of a pad with a stiffer anterior leading edge created by packing more material into the anterior edge or pressing the anterior edge to greater stiffness.
Figure 25:
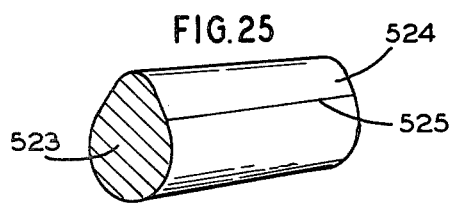
FIG. 25 is a perspective view of a completed wrapped pad with the edges of the wrapping bonded.
Figure 27:
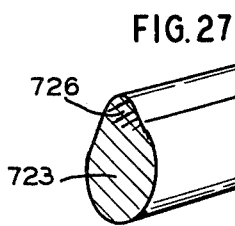
FIG. 27 is a perspective view of a pad with a narrow anterior leading edge created by pressing the anterior edge.

A critical problem is to provide a proper anterior leading edge like 15, 115 and 315 so that the pad can readily be inserted by the user. This can be accomplished in several ways. First, by packing the filler material more densely into the anterior portion 626 as shown in FIG. 26, and second, by pressing the anterior portion to a harder consistency, 626 and 726 as shown in FIGS. 26 and 27. If the filler is pre-pressed, it can be prepared before the wrapping is applied. If the filler is loose the pressure can be applied to create the anterior edge after wrapping is applied. The anterior edge must be stiffer and preferably smaller than the body of the posterior portion of the pad so as to facilitate insertion into the interlabial space. Also, the anterior edge may be identified by a colored line on the outer surface of the pad. Other methods may be readily used to provide a stiffer anterior edge since it is mainly a matter of degree.

Pads made of pressed material such as pressed cotton, cellulose, rayon, polyester or other synthetic materials with anterior leading edges created as in FIGS. 26 or 27 and indicated by numbers 626 and 726, can be used as such without requiring an outer wrapping.

Figure 28:
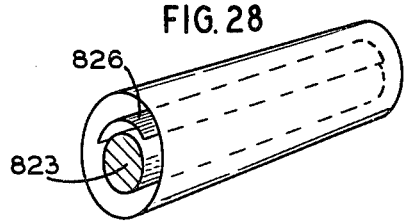
FIG. 28 is a perspective view of a pad with a stiffer concave strip incorporated under the anterior edge of the wrapping.
Figure 29:
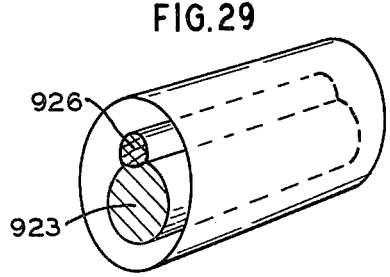
FIG. 29 is a perspective view of a pad with a tubular stiff strip incorporated under the anterior edge of the wrapping.

A stiffer strip 826 of cellulose, pressed cotton, pressed rayon, pressed polyester, plastic or the like can be placed under the anterior edge with the filler 823, as shown in FIG. 28. The filler 823 and strip 826 can then be wrapped with the outer wrapping to complete the long geometric form. Instead of the channel-like stiffer strip 826 shown in FIG. 28, a thinner or narrower stiffer strip of round, oval or polygonal cross-section 926 may be placed on top on the filler core 923 and wrapped with the outer wrapping material as shown in FIG. 29. The long pads are then cut transversely into about two inch lengths to create the final pads. The stiffer strips may also be incorporated into pressed cores to make wrapped or unwrapped pads.

The embodiment of the invention in which an exclusive property or privilege is claimed are defined as follows:

1. A method of making feminine hygienic pads from a material of predetermined width by
    folding said material producing opposed longitudinal edge portions and opposed faces,
    said longitudinal folds providing a folded geometric form,
    said method including the forming of a first panel by one or more inwardly directed folds of said material of one longitudinal edge portion over one face of said material providing a fold formed anterior leading edge, forming a second panel by one or more inwardly directed folds of the material of the other longitudinal edge portion over one face thereof, folding said second panel across a major portion of the width of the one face and over said first panel to a point short of the anterior leading edge formed during the folding of said first panel, bonding the forward folded edge of said second panel to the underlying material of said first panel inwardly of said anterior leading edge of said first panel to define an anterior portion with a leading anterior edge and a larger posterior portion.

2. The method as in claim 1 wherein said bonding is by means of an adhesive.

3. The method as in claim 1 wherein said bonding is by means of crimping.

4. The method as in claim 1 wherein said bonding is by means of heat.

5. The method as in claim 1 wherein said bonding is by means of pressure.

6. The method as in claim 1 wherein said bonding is by ultrasonic means.

7. The method as in claim 1 wherein a filler material is inserted between the folds of the folded material prior to bonding.

8. The method as in claim 1 including the cutting of said folded material transverse to the folds to provide pads of predetermined length.

9. A method as in claim 1 wherein a filler material is introduced into folded material whose free edges are joined to create a tubular form containing said filler material wherein the opposed surfaces of the tubular form are then bonded together by ultrasonic means at a point near one of the edges of the tubular form to create a long geometric form with an anterior leading edge and a larger posterior portion.

10. The method as in claim 1 wherein a filler material in the form of a prepressed ribbon is inserted between the folds of the folded material prior to bonding.

11. A method of making feminine hygienic pads from a material of predetermined width with opposed longitudinal edge portions and opposed faces by folding said material into longitudinal folds providing a folded form, said method including forming a first panel by one or more inwardly directed folds of one longitudinal edge portion over a minor portion of the width of one face of said material to provide a fold formed anterior leading edge and a following edge, forming a second panel by one or more inwardly directed folds of the other longitudinal edge portion over said one face, folding said second panel across a major portion of the width of the one face and into abutment with the following edge of said first panel, bonding the forward folded edge of said second panel to the following edge of said first panel by known means of the use of adhesive, crimping, heat, pressure, ultrasonic means, or the like to define an anterior portion with a leading anterior edge and a larger posterior portion.

12. The method as in claim 11 wherein a filler material is inserted between the folds of the folded material prior to bonding.

13. The method as in claim 11 including the cutting of said folded material transverse to the folds to provide pads of predetermined length.

14. The method as in claim 9 wherein a filler material in the form of a prepressed ribbon is inserted between the folds of the folded material prior to bonding.

15. A method of making feminine hygienic pads with an anterior edge from a material of predetermined width by folding said material over a filler material and including the step of placing a stiffer strip of material under the anterior edge, and bonding the free edge of the folded material to provide a longitudinal geometric form with a stiffer anterior leading edge.

16. The method as in claim 15 including the cutting of said longitudinal form transverse to the folds to provide pads of predetermined length.

17. A method of making feminine hygienic pads, with an anterior edge capable of being inserted into the interlabial space, from prepressed material and including the step of inserting a stiffer strip under the anterior edge to provide a longitudinal geometric form with a stiffer anterior leading edge.

18. The method as in claim 17 including the cutting of said longitudinal form transversely to provide pads of predetermined length.

* * * * *